United States Patent
Schmidt

(10) Patent No.: US 9,494,418 B2
(45) Date of Patent: Nov. 15, 2016

(54) 3D DENTAL CAMERA FOR RECORDING SURFACE STRUCTURES OF AN OBJECT MEASURED BY MEANS OF TRIANGULATION

(75) Inventor: Volker Schmidt, Berlin (DE)

(73) Assignee: SIRONA DENTAL SYSTEMS, GmbH, Bensheim (DE)

( * ) Notice: Subject to any disclaimer, the term of this patent is extended or adjusted under 35 U.S.C. 154(b) by 1160 days.

(21) Appl. No.: 13/055,959

(22) PCT Filed: Aug. 3, 2009

(86) PCT No.: PCT/EP2009/059991
§ 371 (c)(1),
(2), (4) Date: Jun. 13, 2011

(87) PCT Pub. No.: WO2010/012838
PCT Pub. Date: Feb. 4, 2010

(65) Prior Publication Data
US 2011/0242281 A1  Oct. 6, 2011

(30) Foreign Application Priority Data

Aug. 1, 2008 (DE) .................. 10 2008 040 947

(51) Int. Cl.
| | |
|---|---|
| A61B 1/06 | (2006.01) |
| G01B 11/25 | (2006.01) |
| A61C 19/04 | (2006.01) |
| A61C 9/00 | (2006.01) |

(52) U.S. Cl.
CPC ............. G01B 11/25 (2013.01); A61C 9/0053 (2013.01); A61C 19/04 (2013.01)

(58) Field of Classification Search
CPC .................. A61B 5/0088; G02B 13/22; H01J 2237/04928
See application file for complete search history.

(56) References Cited

U.S. PATENT DOCUMENTS

| | | |
|---|---|---|
| 4,837,732 A | 6/1989 | Brandestini et al. |
| 5,372,502 A | 12/1994 | Massen et al. |
| 6,359,680 B1 | 3/2002 | Rubbert |

(Continued)

FOREIGN PATENT DOCUMENTS

| | | |
|---|---|---|
| DE | 90 13 454 U1 | 1/1992 |
| DE | 38 29 925 C2 | 3/1994 |

(Continued)

OTHER PUBLICATIONS

J. Zimmermann, "Seminarvortrag zum Thema Optische Mikroskopie," Universitaet Regensburg, Oct. 23, 2003, pp. 1-22 (with a machine-generated translation of the whole document, and a certified translation of Section 4.1).

(Continued)

*Primary Examiner* — Christopher Findley
(74) *Attorney, Agent, or Firm* — Fitzpatrick, Cella, Harper & Scinto

(57) ABSTRACT

A 3D dental camera for recording surface structures of an object by means of triangulation. The camera includes a light source for producing an illumination beam, means for focusing the illumination beam onto the surface of the object, an image sensor for recording a monitoring beam that is the illumination beam reflected by the surface of the object, and means for focusing the monitoring beam onto the image sensor. The light source is subdivided into a plurality of regions that can be independently regulated in terms of light intensity, such that a light center of the illumination beam changes in at least two switching modes of the light source.

16 Claims, 2 Drawing Sheets

(56) References Cited

U.S. PATENT DOCUMENTS

| | | | |
|---|---|---|---|
| 6,885,464 B1 * | 4/2005 | Pfeiffer et al. | 356/602 |
| 7,469,834 B2 | 12/2008 | Schelinski et al. | |
| 8,125,709 B2 * | 2/2012 | Hoering et al. | 359/385 |
| 2005/0090749 A1 | 4/2005 | Rubbert | |

FOREIGN PATENT DOCUMENTS

| | | |
|---|---|---|
| DE | 196 36 354 A1 | 3/1998 |
| DE | 197 42 264 A1 | 4/1999 |
| DE | 198 29 278 C1 | 2/2000 |
| DE | 10 2005 002 190 A1 | 7/2006 |
| EP | 0 250 993 B1 | 11/1991 |
| WO | 98/11403 A1 | 3/1998 |

OTHER PUBLICATIONS

German Patent Office, Official Communication dated Nov. 10, 2009, 3 pages (with a machine-generated translation), issued in German counterpart application.

* cited by examiner

3D DENTAL CAMERA FOR RECORDING SURFACE STRUCTURES OF AN OBJECT MEASURED BY MEANS OF TRIANGULATION

The invention relates to a 3D dental camera for recording surface structures of an object to be measured, using triangulation. The 3D dental camera comprises a light source for producing an illuminating beam, means for focusing the illuminating beam onto the surface of the object to be measured, an imaging sensor for recording an illuminating beam reflected by the surface of the object to be measured to form a monitoring beam, and means for focusing the monitoring beam onto the imaging sensor. In the triangulation method, the spatial position of the object to be measured is determined with reference to a known distance between the light source and the imaging sensor, a so-called triangulation baseline, to a first triangulation angle between the illuminating beam and the triangulation baseline and to a second triangulation angle between the monitoring beam and the triangulation baseline.

PRIOR ART

A number of 3D dental cameras are known from the prior art which make it possible to measure surface structures of objects to be measured, such as teeth of a patient, by means of triangulation.

DE 198 29 278 C1 discloses a 3D camera for recording surface structures, more particularly for dental purposes. This 3D camera comprises means for producing a light beam, which can be guided onto an object to be measured from a first direction via a projection optical path, the reflected light beam being guided through a monitoring optical path to an imaging sensor for reception of the reflected light. The centroid beam of the projection optical path and that of the monitoring optical path enclose a triangulation angle. Furthermore, means are present in the projection optical path for producing a reference pattern, and means are provided in the projection and/or monitoring optical paths for altering the triangulation angle. A variable, asymmetric diaphragm, a shading plate, particularly in the form of a vane driven by a solenoid, or a diaphragm comprising liquid crystals are disclosed as the means placed in the projected optical path for altering the triangulation angle. The triangulation angle is thus altered by means of asymmetric partial shading of the light source caused by shifting the centroid beam in the projected optical path. Furthermore, the centroid beam of the monitoring optical path can likewise be shifted by means of partial shading so that the triangulation angle is altered. This shading can be achieved, for example, by means of mechanically driven vanes in the monitoring optical path, which vanes can partially shade the luminous field of the monitoring beam.

A disadvantage of this 3D camera is that the light source is partially switched off or shaded for altering the triangulation angle, with the result that the luminous intensity of the illuminating beam is reduced. Consequently, the contrast of the image created is reduced and the measurement accuracy is thus impaired.

A further drawback is that the illuminated pupil must have a relatively extensive spatial expanse to make it possible to achieve the desired alteration of the triangulation angle by shading said illuminated pupil.

DE 10 2005 002 190 Al discloses a scanner and a method for operating a scanner, the scanner comprising a projector for detecting a surface relief of an object, the projector being configured to guide a light beam from the projector across the surface relief in order to obtain an illuminated area on the surface relief. The scanner further comprises a collector comprising a collector micromirror that can be stimulated to oscillate in two dimensions, and a punctiform light detector, the collector micromirror being disposed for oscillation in a first direction parallel to the line of illumination and in a second direction, differing from the first, such that a reflection of the illuminated area within a scan area of the microscanner mirror can be imaged by the same on the punctiform light detector, and the collector being adapted to output a detector signal, from which a position of the illuminated area in the first and second directions is derivable. The alteration of the triangulation angle between the illuminating beam and the reflected beam is achieved by means of the oscillation of the collector micromirror in order to scan a defined portion of the surface relief of the object to be measured.

A drawback of this scanner is that the alteration of the triangulation angle is achieved by way of oscillation of a collector micromirror. The inertia of the collector micromirror restricts the maximum frequency of alteration of the triangulation angle. Furthermore, the control of a mechanically driven collector micromirror involves extensive engineering effort.

EP 0 250 993 Al discloses a 3D camera, which, for determining the differences in height or depth of the surface structure, comprises means for producing a reference pattern that can be projected onto the surface structure. With the aid of the image data recorded by means of an imaging sensor and with the use of a method referred to as the "phase-shifting method", the surface structure is analyzed in terms of differences in height and depth and the spatial surface structure is presented as a three-dimensional image. The linear reference pattern projected onto the object to be measured is produced by an LCD system or a mechanical grid. The unambiguous range, i.e., the range in which the height difference between two object points can be unambiguously recorded, is predefined by the distances between the individual lines of the reference pattern. The unambiguous range is the depth range in which a period of the grating is imaged via the triangulation angle.

This device suffers from the drawback that the height information of points on the surface structure located in the shadow region of the projected reference pattern cannot be measured. In the case of a convexly shaped surface structure, the shadow region can be formed on that side of the object that is remote from the light beam.

DE 90 134 54 U1 discloses a 3D camera in which means for producing a first reference pattern and a second reference pattern are present in the projected optical path in order to enlarge the unambiguous range.

A disadvantage of this device is that the two reference patterns can be superimposed and thus measurement errors can be caused. Furthermore, the engineering effort involved is relatively high.

A second group of light beams is further proposed, which can be guided onto the object to be measured from a second direction, differing from the first, via a further projected optical path. Hence the surface structure can be illuminated from different directions.

A disadvantage of this device is that the arrangement of a second light source with means for producing a second reference pattern demand high engineering effort and result in greater dimensions and increased weight of the 3D dental camera. This is a drawback for hand-held 3D dental cameras in particular.

WO 98/11403 A1 discloses a device for the three-dimensional measurement of objects. The projection unit for producing the reference pattern and the recording unit for recording the reflected beam are designed as separate units and can be positioned or guided during the measurement process independently of one another. The triangulation angle can thus be altered in an arbitrary manner.

A disadvantage of this device is that the mechanical alteration of the position of the projection unit and the recording unit can be carried out only at a frequency determined by the inertia of the projection unit and recording unit moved.

Furthermore, the effort required for operating the device is relatively high and this method is not suitable for a hand-held 3D dental camera. Moreover, the 3D dental camera has to be recalibrated when a position is altered. Thus it is an object of this invention to provide a 3D dental camera which makes it possible to alter the triangulation angle rapidly at a low equipment outlay and with a high degree of precision.

SUMMARY OF THE INVENTION

This object is achieved by the features defined in the claims. The 3D dental camera of the invention for recording surface structures of an object to be measured by means of triangulation comprises a light source for producing an illuminating beam, means for focusing the illuminating beam onto the surface of the object to be measured, an imaging sensor for recording an illuminating beam reflected by the surface of the object to be measured to form a monitoring beam, and means for reproducing the monitoring beam on the imaging sensor. The light source is subdivided into a plurality of regions that can be regulated independently of each other in terms of the luminous intensity thereof such that a light center of the illuminating beam is altered in at least two switching modes.

The 3D dental camera of the invention is suitable for recording spatial surface structures by means of triangulation. In a triangulation measuring method, the surface of an object to be measured is scanned by an illuminating beam, and the illuminating beam reflected by the object to be measured in the form of a monitoring beam is recorded by an imaging sensor. The spatial position of the monitored point of measurement on the surface of the object to be measured relative to the triangulation baseline is determined with reference to the known distance between the light source and the imaging sensor, a so-called triangulation baseline, a known angle between the triangulation baseline and the illuminating beam, and a known angle between the triangulation baseline and the monitoring beam.

Means for focusing the illuminating beam comprise means that configure the size of a pupil of the illuminating beam. The size of the pupil of the illuminating beam can be delimited by means such as a diaphragm, an optical system providing an intermediate image of a diaphragm or by borders of lenses in the illuminating beam path.

The pupil defines the area to be considered when calculating the light center of the illuminating beam, and its intensity is predefined by the light source, such as an LED.

A diaphragm is used in the optical path of the monitoring beam in order to narrow down the monitoring beam to the diameter of the diaphragm and to define the direction of the monitoring beam. In the case of diffuse reflection, the illuminating beam is reflected in all directions so that the direction of the monitoring beam is specified by the position of the diaphragm.

For accelerating the triangulation measuring method, a so-called stripe projection method can be used. Here, a pattern, for example in the form of parallel stripes, is projected onto the object to be measured. This object is illuminated sequentially with the aid of a projected pattern. The imaging sensor registers the projected pattern at a known angle to the triangulation baseline, so that a chronological sequence of different brightness values is produced for every pixel of the imaging sensor. It is thus possible, by means of the stripe projection method, to simultaneously determine the spatial position of a plurality of measured points illuminated by the projected pattern. The surface of the object to be measured thus need not be scanned pointwise by a punctiform illuminating beam, but instead, the points in a two-dimensional area are scanned simultaneously.

The light source of the invention is subdivided into a plurality of regions, which makes it possible to shift the light center of the illuminating beam by controlling these regions. A light center is a centroid of a cross-section of the illuminating beam weighted by the intensity. An illuminating beam having a circular cross-section and an intensity diminishing toward the edge would thus have its light center at the center on the axis of symmetry of the illuminating beam. The intensity can also diminish uniformly toward the edge.

By altering the light center, the illuminating beam is caused to illuminate the object to be measured from a different angle. Alteration of the light center thus results in an alteration of the triangulation angle. Multiple measurements at different triangulation angles result in an increase in the unambiguous range and therefore make it possible to carry out depth measurements over an extended depth range.

The known methods for shifting the light center involve, on the one hand, mechanical displacement of the light source and, on the other hand, partial shading of the illuminating beam by means of asymmetrical diaphragms, for example. Compared with these known methods, the advantage of the present invention is that the light center is shifted solely by electronic control of the different regions of the light source without the use of mechanical means that have a relatively long switching time and are more prone to errors.

Advantageously, illumination by means of the illuminating beam can be achieved by means of Kohler illumination, by means of which the light source is imaged sharply in the plane of an aperture diaphragm.

Kohler illumination makes it possible to independently regulate the diameter of the illuminated zone and the numerical aperture of the illumination. A construction comprising two convex lenses, namely a collector lens and a condenser lens, and two diaphragms, namely a luminous-field diaphragm and an aperture diaphragm are used for this purpose. The collector lens sharply images the light source disposed upstream thereof in the plane of the aperture diaphragm, and the aperture diaphragm is present in the focal plane of the condenser lens. The beams emanating from a point in the aperture diaphragm thus become parallel beams in the plane of the object. The distance between the condenser lens and the plane of the object is chosen such that the luminous-field diaphragm is sharply imaged in the plane of the object. The diameter of the illuminated zone in the plane of the object can be regulated by adjusting the luminous-field diaphragm. The aperture diaphragm controls the angle of incidence at which the light beams reach the plane of the object, and thus also the numerical aperture of the illumination.

Advantageously, the light source can be subdivided into at least three regions. As a result, the luminous intensity of three regions can be regulated independently of each other in order to shift the light center. The three regions can be juxtaposed in a row.

Advantageously, the light source can be switched between at least two modes, such that any one region of the light source can be switched off in each mode while the remaining at least two adjacent regions are switched on.

The first and second regions of the light source are switched on in the first switching mode, and the second and the third regions are switched on in the second switching mode. The light center of the illuminating beam is located between the regions that are switched on and is shifted when switching from one mode to the other. The advantage here is that the illuminating beam results from superimposition of light beams from the two regions that are switched on and thus has a relatively high luminous intensity. This relatively high luminous intensity, when compared with the luminous intensity of only one region, results in better detection of the monitoring beam by the imaging sensor and thus higher measurement accuracy. There is only a small gap between the adjoining regions of the light source that are switched on so that the distribution of the luminous intensity remains almost homogeneous over the entire surface of the light source.

Advantageously, the light source can be switched between at least three modes, any one region of the light source being switched on in each mode while the remaining at least two regions are switched off.

The first region of the light source is switched on in the first switching mode, the second region is switched on in the second switching mode, and the third region is switched on in the third switching mode. Hence the illuminating beam is always produced by a single region. As a result, the width of an individual region represents the width of the light source. A smaller width of the light source results in fewer half-shade effects so that the measurement accuracy is increased. The half-shade effects result from the fact that the edge of the aperture diaphragm is illuminated by one edge of the light source and the opposite edge of the light source so that a half-shade is formed behind the aperture diaphragm between the shaded region and the region having maximum intensity, which half-shade is relatively broad when the light source has a large width. Furthermore, the changeover between the switching modes results in a shift of the light center by a distance equal to the distance between the respective regions of the light source. As a result, a greater displacement of the light center and thus a greater alteration of the triangulation angle is achieved than when a changeover between switching modes is carried out in which two regions are switched on at the same time.

Advantageously, the light source can be subdivided into at least two regions. This thus makes it possible to change over between two switching modes in order to alter the triangulation angle.

Advantageously, the light source can be switched between two modes in which any one region of the light source is switched on in each mode. As a result, the light center of the illuminating beam is shifted by the distance separating the two regions when there is a changeover from the first to the second mode.

Advantageously, the regions of the light source can be switched on and off. As a result, the light center of the illuminating beam assumes defined positions in the individual switching modes.

Advantageously, the regions can be continuously variable in terms of their luminous intensity. As a result, the luminous intensity of the illuminating beam can be regulated. If the illuminating beam is produced as a result of the overlap of light beams from a plurality of regions, the light center can be shifted slightly by changing the ratio of the luminous intensities of the individual light beams.

Advantageously, means for producing a projected pattern onto the surface of the object to be measured can be placed in the optical path of the illuminating beam. As a result, a pattern can be projected onto the object to be measured in order to apply the stripe projection method mentioned above. The advantage of the stripe projection method is that the information relating to the spatial position of the object to be measured can be ascertained more rapidly than by means of a spot scan of the object.

Advantageously, the shift of the light center of the illuminating beam between two switching modes of the light source can change a triangulation angle between the illuminating beam and the monitoring beam by from 0.7° to 1.3°. Hence the change in the triangulation angle is sufficient to illuminate teeth having typical cavities and to considerably improve the accuracy of measurement.

Advantageously, the separate regions of the light source can be formed by a plurality of LEDs. LEDs are compact, durable, and energy-saving light sources that are easy to regulate in terms of their luminous intensity. Therefore, LEDs are suitable to particular advantage for use as regions of the light source of the invention.

Advantageously, the separate regions of the light source can be disposed in a row at right angles to the illuminating beam and in a triangulation plane.

This is an arrangement of the separate regions that makes it possible to alter the triangulation angle most effectively. If only one region remains switched on at any one time in the different switching modes, the light center will be shifted by the distance between the respective regions when there is a changeover between switching modes. The separate regions are disposed in the triangulation plane, the triangulation plane being defined by the illuminating beam and the monitoring beam. Hence the desired effect, namely a maximum shift of the light center, is achieved particularly advantageously, as opposed to a triangular arrangement of the regions, for example.

Advantageously, the separate regions of the light source can have a rectangular shape and can be directly juxtaposed. Hence in the case of a mode in which a plurality of regions is switched on, there are only small gaps between them so that the luminous intensity produced by the combined separate regions shows an almost homogenous distribution of luminous intensity. A homogenous distribution of the luminous intensity in the pupil results in a homogenous distribution of the illumination of the measured area, which is of particular advantage in a triangulation method, since the object to be measured is illuminated uniformly.

These rectangular regions can be LEDs having rectangular light-emitting surfaces, to which the fluorescent layer has been applied uniformly in a rectangular shape. Alternatively, large-area LEDs having a uniformly applied fluorescent layer of arbitrary shape can be used in conjunction with rectangular diaphragms.

Advantageously, the overall luminous intensity of the light source can remain unaltered between the different switching modes. As a result, the surface of the object to be measured will be illuminated by a constant overall luminous intensity in the different modes. The advantage in this case is that the evaluation of the image data does not necessitate any corrections with regard to the luminous intensity.

Advantageously, in addition to the modes having constant overall luminous intensity, in which defined regions of the light source are switched off, the light source can be switched over to a mode in which all of the regions of the light source are switched on. As a result, an additional mode having higher luminous intensity is provided, in which the triangulation angle of the centroid beam differs from the triangulation angles in the other modes. In this additional mode, the CCD sensor can, due to the higher luminous intensity, be subjected to a shorter exposure time to bring the image signal into the detection range specific to the CCD sensor. The image data generated are then calibrated allowing for the higher luminous intensity and the shorter exposure time and used with the image data generated from the images created in the other modes for calculations within the scope of the triangulation method.

BRIEF DESCRIPTION OF THE DRAWINGS

Exemplary embodiments of the invention are shown in the drawings, in which.

EXEMPLARY EMBODIMENT

Figure 1:
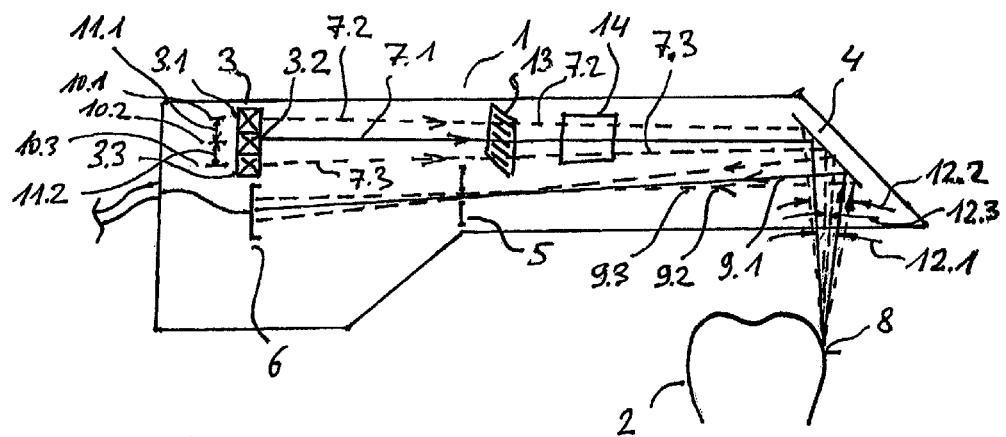
FIG. 1 shows a dental camera for recording surface structures of an object to be measured.

FIG. 1 shows a dental camera 1 for recording surface structures of an object 2 to be measured, which is in the case illustrated a single tooth. The 3D dental camera 1 comprises a light source 3, a beam-deflecting mirror 4, a diaphragm 5, and an imaging sensor 6. The light source 3 comprises three LEDs 3.1, 3.2, and 3.3, which represent regions of the light source 3 that can be regulated independently of each other. The light source 3 produces an illuminating beam 7, which is deflected by means of the beam-deflecting mirror 4 toward the surface 8 of the object 2 to be measured. The illuminating beam 7 is reflected by the surface 8 of the object 2 to be measured to form of a monitoring beam 9. The surface 8 of a tooth resembles a Lambert body so that the monitoring beam 9 is mainly produced as a result of diffuse reflection according to Lambert's Law.

The monitoring beam 9 passes through the diaphragm 5 and impinges on the imaging sensor 6. The diaphragm 5 is a pinhole that allows only a narrow beam to pass toward the imaging sensor 6. The imaging sensor 6 records the monitoring beam 9 and transmits the image information to an image evaluation unit (not shown).

The light source 3 illustrated has three different switching modes, the central LED 3.2 being switched on while the remaining LEDs 3.1 and 3.3 are switched off, in the first switching mode. In the second switching mode, the first LED 3.1 is switched on, and the second LED 3.2 and the third LED 3.3 are switched off. In the third switching state, the third LED 3.3 is switched on, and the first LED 3.1 and the second LED 3.2 are switched off. The illuminating beam 7.1 and the monitoring beam 9.1 in the first switching mode are shown as continuous lines, the illuminating beam 7.2 and the monitoring beam 9.2 are shown as dashed lines, and the illuminating beam 7.3 and the monitoring beam 9.3 are like-wise shown as dashed lines.

The illuminating beam 7 can have a light center that is disposed symmetrically relative to the intensity distribution and in the region of maximum intensity.

A light center is a centroid of a cross-section of the illuminating beam weighted by the intensity. An illuminating beam having a circular cross-section and an intensity diminishing toward its circumference would thus have its light center at the center, that is, in the axis of symmetry of the illuminating beam.

In the first switching mode, the light center 10.1 is located at the center of the first LED 3.1, the light center 10.2 in the second switching mode is located at the center of the second LED 3.2, and the light center 10.3 in the third switching mode is located at the center of the third LED 3.3. By changing the switching modes, the light center 10 of the illuminating beam 7 is thus shifted by a distance 11.1 between the first light center 10.1 and the second light center 10.2, and by a distance 11.2 between the second light center 10.2 and the third light center 10.3. The shift of the light center results in a change in the triangulation angle 12. The triangulation angle 12 is the angle enclosed by the illuminating beam and the monitoring beam 9. In FIG. 1, the triangulation angle 12.1 is that obtained in the first switching mode, the triangulation angle 12.2 is that obtained in the second switching mode and the triangulation angle 12.3 is that obtained in the third switching mode.

The device illustrated makes it possible to change the triangulation angle 12 in a simple manner exclusively by controlling the three LEDs and without the use of mechanical means such as mechanically adjustable diaphragms or vanes. Images of one and the same object 2 to be measured are created by means of the device of the invention in the three different states from three slightly displaced directions of illumination. The monitoring direction remains unchanged. When there is a change in the triangulation angle 12, the monitoring beams reflected from different points on these surfaces are not superimposed on each other on the imaging sensor 6, but instead, they impinge on the imaging sensor 6 at discrete locations. The spatial position of these points is computed from the image information provided by the imaging sensor 6. As matching methods for combining a plurality of images in a common coordinate system, methods are used in which punctiform markers are attached to the object to be measured as congruent points of the different images, and the different images are superimposed with reference to these markers or the different images can be superimposed with reference to characteristic features of the object to be measured such as eminences, depressions, or characteristic shapes. The recognition of three punctiform markers or three congruent characteristic features of the object to be measured provides sufficient information for superimposing the spatial images.

Means 13 for producing a reference pattern in the form of a parallel line pattern is illustrated in the optical path of the illuminating beam 7. The means 13 is a grid comprising parallel slits disposed at right angles to the linear orientation of the three LEDs 10.1, 10.2, and 10.3. Thus, when there is a change in the triangulation angle 12, the line pattern is shifted in a direction extending perpendicularly to the lines. In the triangulation method, the object to be measured is scanned sequentially in time with this line pattern. When evaluating the image information provided by the imaging sensor 6 in the form of a temporal sequence of different brightness values, each monitoring beam 9 must be assigned to the respective light stripe of the light pattern. The assignment can be carried out by means of a gray code method in that each light stripe contains a binary code of different brightness values representing the number of the stripe. A higher degree of precision can be achieved using the phase shifting method, since it allows for the assignment of a non-discrete coordinate.

Figure 2:
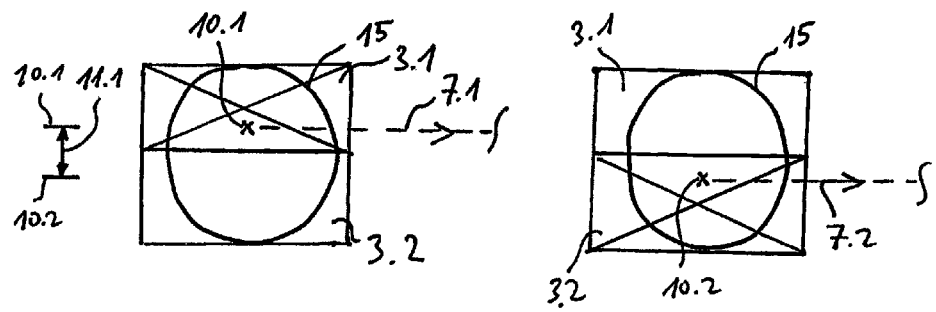
FIG. 2 shows another embodiment of the light source comprising two LEDs in two switching modes.

Furthermore, an objective 14 is disposed in the optical path of the illuminating beams 7.1, 7.2, and 7.3 as means for focusing the beams onto the object 2 to be measured. FIG. 2 shows another embodiment of the light source 3 comprising two rectangular LEDs 3.1 and 3.2, which are directly juxtaposed and are disposed in a row in a triangulation plane (not shown), which triangulation plane is defined by the illuminating beam 7 and the monitoring beam 9. These rectangular LEDs 3.1 and 3.2 have a fluorescent layer that is applied evenly in order to ensure homogeneous distribution of the luminous intensity. The pupil 15 of the entire optical system in the illuminating beam path is shown as a circular area. The size of the pupil of the illuminating beam can be defined with the aid of means disposed in the path of the illuminating beam, such as a diaphragm, an optical system comprising an intermediate image of a diaphragm or borders of lenses.

The pupil defines the area to be allowed for when calculating the light center of the illuminating beam, and the intensity is predefined by the light source, such as an LED.

The light source 3 can be regulated between two switching modes. In the illustration on the left-hand side, the light source is shown in the first switching mode, in which the first rectangular LED 3.1 is switched on and the second LED 3.2 is switched off. In the first switching mode, the light center 10.1 of the illuminating beam 7.1 is located in the upper half of the pupil 15 that is illuminated by the first. LED 3.1. It is shown diagrammatically that the first illuminating beam 7.1 issues from the light center 10.1. The illustration on the right-hand side shows the light source 3 in the second switching state, in which the second LED 3.2 is switched on and the first LED 3.1 is switched off. In the second switching mode, the light center 10.2 of the illuminating beam 7.2 is located in the lower half of the pupil 15 that is illuminated by the second LED 3.2. It is shown diagrammatically that the second illuminating beam 7.2 issues from the second light center 10.2. When switching the light source from the first switching mode to the second switching mode, the light center is thus shifted by a distance 11.1 with the result that the triangulation angle 12 shown in FIG. 1 is altered.

Figure 3:
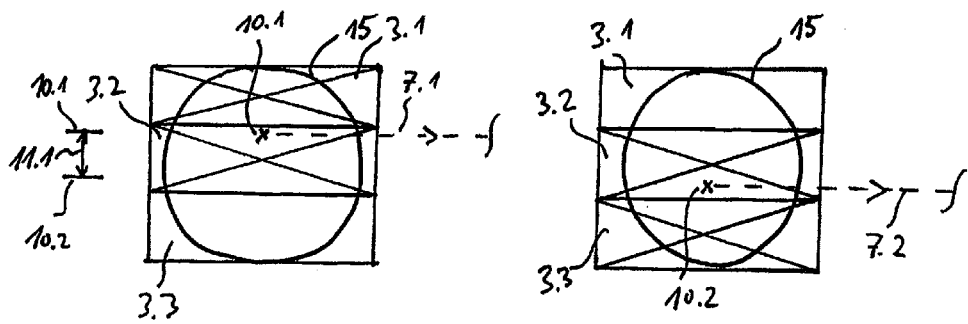
FIG. 3 shows a further embodiment of the light source 3 comprising three LEDs in two switching modes.

FIG. 3 shows another embodiment of the light source 3, comprising three LEDs 3.1, 3.2, and 3.3, having two switching modes. The illustration on the left-hand side shows the light source in the first switching mode, in which the LEDs 3.1 and 3.2 are switched on and the third LED 3.3 is switched off. The second illustration shows the light source in the second switching state, in which the first LED 3.1 is switched off and the LEDs 3.2 and 3.3 are switched on. The LEDs 3.1, 3.2, and 3.3 are rectangular, as shown in FIG. 2, and have a homogeneously distributed luminous intensity. In both switching modes, two LEDs are switched on at any one time so that the overall luminous intensity of the light source 3 remains constant in both switching modes. The pupil 15 of the entire optical system in the illuminating beam path is shown as a circular area. The light center 10.1 in the first switching mode of the illuminating beam 7.1 is located above the center of the pupil 15, in the region of the pupil 15 that is illuminated by the first LED 3.1 and the second LED 3.2. As a result of the overlap of the light beams the first LED 3.1 and the second LED 3.2, the illuminating beam 7.1 has a cross-section corresponding to a portion of the circular pupil 15. In the second switching mode, the light center 10.2 of the illuminating beam 7.2 is located below the center of the pupil 15, in the lower region of the pupil 15 that is illuminated by the second LED 3.2 and the third LED 3.3. When the light source is switched from the first to the second switching mode, the light center is shifted by the distance 11.1. The triangulation angle 12 shown in FIG. 1 is also altered as a result of the change in position of the light center.

Figure 4:
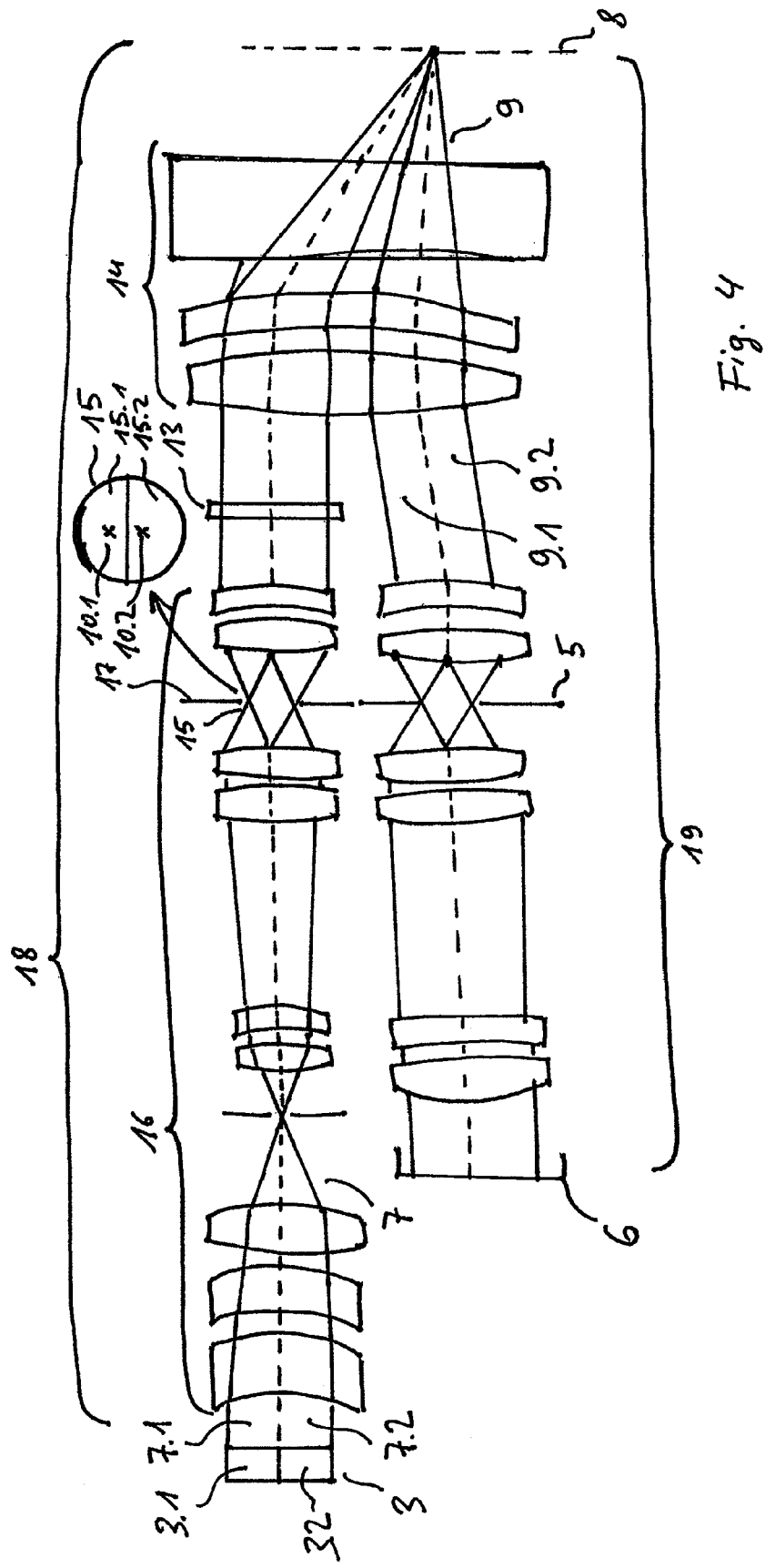
FIG. 4 is a detailed illustration of the optical arrangement of the dental camera.

FIG. 4 is a detailed illustration of the optical system of the dental camera 1. The light source 3 comprises a first rectangular LED 3.1 and a second rectangular LED 3.2, the two LEDs being directly juxtaposed in a row in the triangulation plane 16. The triangulation plane 16 is defined by the illuminating beam 7 and the monitoring beam 9. In the first mode, the first LED 3.1 emits a first illuminating beam 7.1, and in the second mode, the second LED 3.2 emits a second illuminating beam 7.2. The illuminating beams 7.1 and 7.2 pass through a Kohler optical system 16 to achieve Kohler illumination with the light source 3 being imaged in the plane of an aperture diaphragm 17. This image of the light source 3 in the plane of the aperture diaphragm 17 forms the pupil 15 of an illuminating beam path 18. Furthermore, the illuminating beams 7.1 and 7.2 pass through the grid 13 comprising parallel slits, and a striped pattern is produced, which is projected onto the surface 8 of the object 2 to be measured by means of the objective 14 comprising a plurality of lenses. In the first mode, the upper region of the pupil 15.1 is illuminated, and the light center 10.1 is located above the center of the pupil 15. In the second mode, the lower region of the pupil 15.2 is illuminated, and the light center 10.2 is located below the center of the pupil 15. The illuminating beams 7.1 and 7.2 are reflected by the surface 8 to produce monitoring beams 9.1 and 9.2 which are guided through the objective 14 and additional lens systems toward the imaging sensor 6 and are recorded by the latter. The diaphragm 5 delimits the pupil of the Monitoring beam path 19. The outer borders of the illuminating beams 7.1, 7.2 and the monitoring beams 9.1, 9.2 are shown as continuous lines, and the border between the illuminating beams 7.1, 7.2 and the monitoring beams 9.1, 9.2 is shown as a dashed line.

LIST OF REFERENCE SIGNS 1 dental camera
2 object to be measured
3 light source
3.1 LED
3.2 LED
3.3 LED
4 deflection mirror
5 diaphragm
6 imaging sensor
7 illuminating beam
8 surface
9 monitoring beam
9.1 monitoring beam
9.2 monitoring beam
9.3 monitoring beam
10 light center
10.1 light center
10.2 light center
10.3 light center
11 displacement of the light center
11.1 displacement of the light center
11.2 displacement of the light center
12 triangulation angle
12.1 triangulation angle
12.2 triangulation angle
12.3 triangulation angle 13 grid
14 objective
15 pupil
16 triangulation plane
17 aperture diaphragm
18 optical path of the illuminating beam
19 optical path of the monitoring beam

The invention claimed is:

1. A 3D dental camera, comprising:
a light source comprising a plurality of discrete regions juxtaposed to each other and configured to generate an illuminating beam, wherein a luminous intensity of each of the plurality of regions can be controlled independently;
an objective arranged within the dental camera to focus the illuminating beam generated by the light source onto a surface of an object to be measured;
an imaging sensor arranged within the dental camera to record a monitoring beam formed from a reflection of the illuminating beam by the surface of the object to be measured; and
imaging optics arranged within the dental camera to image the monitoring beam on the imaging sensor,
wherein luminous intensities of the plurality of regions of the light source are electronically controlled to operate in:
  (i) a first switching mode where a light center of the illuminating beam, in a plane of the light source, is at a first location, and
  (ii) a second switching mode where the light center of the illuminating beam, in the plane of the light source, is at a second location that is shifted by a distance from the first location in the plane of the light source,
wherein switching from the first switching mode to the second switching mode such that the light center of the illuminating beam is shifted by the distance alters a triangulation angle between the illuminating beam and the monitoring beam.

2. The 3D dental camera according to claim 1, wherein illumination by the illuminating beam is effected in a manner of Kohler illumination, in which the light source is sharply imaged in a plane of an aperture diaphragm.

3. The 3D dental camera according to claim 1, wherein the plurality of regions of the light source includes at least three regions.

4. The 3D dental camera according to claim 1,
wherein in each of the first switching mode and the second switching mode two adjacent regions, of the plurality of regions of the light source, are switched on and one region, of the plurality of regions of the light source, is switched off.

5. The 3D dental camera according to claim 1,
wherein the luminous intensities of the plurality of regions of the light source are electronically controlled to operate in a third switching mode where the light center of the illuminating beam, in the plane of the light source, is at a third location that is shifted by another distance from the second location.

6. The 3D dental camera according to claim 5, wherein in the first switching mode, the second switching mode, and the third switching mode, one region, of the plurality of regions of the light source, is switched on and at least two regions, of the plurality of regions of the light source, are switched off.

7. The 3D dental camera according to claim 1, further comprising:
a kohler optical system arranged in an illuminating beam path; and
an aperture diaphragm arranged in the illuminating beam path downstream of the kohler optical system in a direction of travel of the illuminating beam,
wherein an image of the light source in the plane of the aperture diaphragm forms a pupil of the illuminating beam path,
wherein, in the first switching mode, the light center of the illuminating beam is located above a center of the pupil, and
wherein, in the second switching mode, the light center of the illuminating beam is located below the center of the pupil.

8. The 3D dental camera according to claim 1, wherein the plurality of regions of the light source are configured to be switched on and off.

9. The 3D dental camera according to claim 1, wherein the plurality of regions of the light source can be continuously brightness-controlled.

10. The 3D dental camera according to claim 1, further comprising:
a pattern production unit disposed in an illuminating beam path and configured to project a pattern onto the surface of the object to be measured.

11. The 3D dental camera according to claim 1, wherein switching from the first switching mode to the second switching mode alters the triangulation angle between the illuminating beam and the monitoring beam by an amount in a range from 0.7° to 1.3°.

12. The 3D dental camera according to claim 1, wherein the plurality of regions of the light source comprises a plurality of LEDs.

13. The 3D dental camera according to claim 1, wherein the plurality of regions of the light source are disposed in a row at right angles to the illuminating beam and are disposed in a triangulation plane.

14. The 3D dental camera according to claim 1, wherein the plurality of regions of the light source are rectangular in shape.

15. The 3D dental camera according to claim 1, wherein an overall luminous intensity of the light source remains constant when switching from the first switching mode to the second switching mode.

16. The 3D dental camera according to claim 1, wherein the light source is further configured to operate in a mode where the plurality of regions of the light source are all on.

* * * * *